United States Patent [19]

Jones

[11] Patent Number: 4,462,800
[45] Date of Patent: Jul. 31, 1984

[54] ORTHODONTIC BITE JUMPING DEVICE

[76] Inventor: Marston Jones, Rainbow Farm, Rte. 1, Box 115C, Salisbury, Md. 21801

[21] Appl. No.: 439,213

[22] Filed: Nov. 4, 1982

[51] Int. Cl.³ .............................................. A61C 3/00
[52] U.S. Cl. ....................................... 433/19; 433/22
[58] Field of Search ...................... 433/19, 22, 21, 18, 433/12, 13

[56] References Cited

U.S. PATENT DOCUMENTS

| | | | |
|---|---|---|---|
| 2,959,856 | 11/1960 | Gurin | 433/22 |
| 3,158,934 | 12/1964 | Waldman | 433/19 |
| 3,238,619 | 3/1966 | Brunson et al. | 433/13 |
| 3,508,332 | 4/1970 | Armstrong | 433/22 |
| 3,618,214 | 11/1971 | Armstrong | 433/19 |
| 3,798,773 | 3/1974 | Northcutt | 433/19 |

FOREIGN PATENT DOCUMENTS

| | | | |
|---|---|---|---|
| 374163 | 4/1923 | Fed. Rep. of Germany | 433/19 |
| 1079955 | 12/1954 | France | 433/19 |

OTHER PUBLICATIONS

"The Mechanism of Class II Correction in Herbst Appliance Treatment", Pancherz, Am. J. Orthed., vol. 82, 8-1982, pp. 104–113.

*Primary Examiner*—John J. Wilson
*Attorney, Agent, or Firm*—LeBlanc, Nolan, Shur & Nies

[57] ABSTRACT

An orthodontic bite jumping device for attachment to orthodontic brace wires affixed to the teeth of the upper and lower jaw of a patient for treatment of overbite. The device includes, for each side of the jaw, a telescope mechanism which is mounted at either end on a respective trunnion member affixed to a brace wire located on the upper and lower teeth. Each trunnion member has a radial slot adjacent the inner end for receiving one of the brace wires. The connection between at least one of the ends of the telescope mechanism and the respective trunnion is such as to provide looseness or "play" in the interaction thereof, making the device more flexible and resilient and thus more durable within the mouth, while at the same time maximizing the comfort of the patient.

15 Claims, 8 Drawing Figures

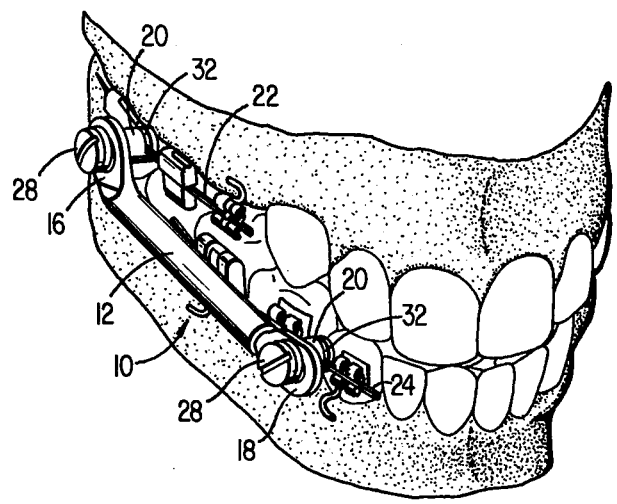
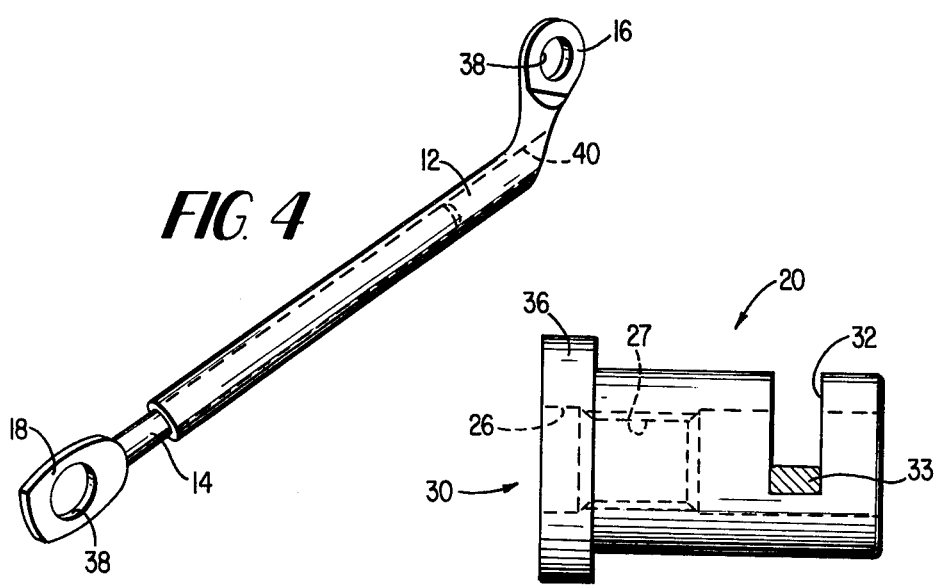

ORTHODONTIC BITE JUMPING DEVICE

BACKGROUND AND SUMMARY OF THE INVENTION

The present invention relates to an orthodontic bite jumping device. More particularly, the present invention is concerned with an orthodontic device which is attached to orthodontic brace wires connected to teeth of the upper and lower jaw for treatment of Class II malocclusions or overbite.

Previous devices for treatment of overbite have included those devices described in the following U.S. Pat. Nos.: 3,618,214 to Armstrong; and 3,798,773 to Northcutt. The Northcutt patent discloses a compression device for use in the realignment of the teeth, including a pair of spring and telescopic tube arrangements which is one embodiment may be attached directly to the brace wire on the upper and lower jaw. The Armstrong patent employs a tension device and includes the use of coiled-wire spring appliances in a tubular casing in which a pair of eyelets are secured at opposite ends of the spring assembly for engagement with hooks on orthodontic arch wires. Armstrong's plural concentric tension springs are intended to provide lateral stability to the coil spring when it is stretched during operation upon opening of the jaws of the patient.

Other prior art devices for use in treatment of overbite have included the Herbst appliance which provides a telescope mechanism to be mounted on either side of the jaw, attached to orthodontic bands which fit around teeth in the upper and lower jaw, for the purpose of maintaining the mandible continuously in an anterior jumped position during all mandibular functions. The previous history of the Herbst appliance has shown that this device is subject to breakage, particularly at the point at which the device is attached to a band which fits around the teeth of the upper or lower jaw. A description of the Herbst appliance is found, for example, in Am. J. Orthod., 82:104-113, 1982, which is incorporated herein by reference.

It is an object of the present invention to provide an improved orthodontic bite jumping device which may be attached directly to the orthodontic brace wires in the upper and lower jaw for treatment of overbite.

It is an additional object of the invention to provide an orthodontic device which is of durable construction so as not to break off in the mouth of the patient during everyday use.

It is a further object of the invention to provide an orthodontic device which is constructed so as to be comfortable in the mouth of the patient and to eliminate various discomforting features of prior art devices.

It is an additional object of the present invention to provide an orthodontic device which remains installed and activated throughout each 24 hour day in treating overbite, while not interfering with chewing or other normal functions of the mouth.

It is another object of the invention to provide continual application of previously determined corrective forces for the purpose of treating a Class II molocclusion.

It is a further object of the invention to provide an orthodontic bite jumping device which is of relatively simple construction, thus facilitating installation of the device in the mouth of the patient.

The foregoing as well as additional objects are attained by the orthodontic bite jumping device of the present invention. The term "bite jumping" as used herein is intended to refer to a change in sagittal intermaxillary dental arch relationships by an anterior displacement of the mandible.

The present device includes a telescope mechanism having an outer tube portion and an inner plunger portion, with the telescope outer tube portion being attached to the upper jaw and the inner plunger portion attached to the lower jaw. Similar telescope mechanisms are positioned on either side of the jaw. Each telescope mechanism is attached to orthodontic brace wires located on the upper and lower teeth by the use of a trunnion or pin having a radial slot therein and an axial opening in the outer end portion. The axial opening, which is in communication with the slot, is for the purpose of receiving a screw member which maintains the device in position on the brace wire.

In the attachment of the telescope tube to the upper jaw, the trunnion is passed through a ring member secured to the outer end of the telescope tube and the trunnion is then positioned so that the upper brace wire is received in the radial slot. A screw member is then passed in friction fitting engagement into the axial opening of the trunnion so as to engage the wire, which is generally of a square cross-section, and thus maintain the wire securely in the slot, at the same time clamping the trunnion to the wire. The trunnion for the lower jaw is passed through a ring located at the outer end of the telescope plunger and is then secured to the brace wire of the lower jaw in a similar manner. The central opening in one or both of the ring members is larger than the diameter of the trunnion passing therethrough so as to provide looseness or "play" during operation of the device.

BRIEF DESCRIPTION OF THE DRAWINGS

FIG. 3 is a perspective view similar to FIG. 2 but with the mouth in the closed position.

FIG. 4 is a perspective view of the telescope tube and plunger members employed in the device of FIG. 1.

FIG. 5 is an enlarged front elevation of the pin or trunnion member employed in the device of FIG. 1.

DESCRIPTION OF THE PREFERRED EMBODIMENTS

Figure 1:
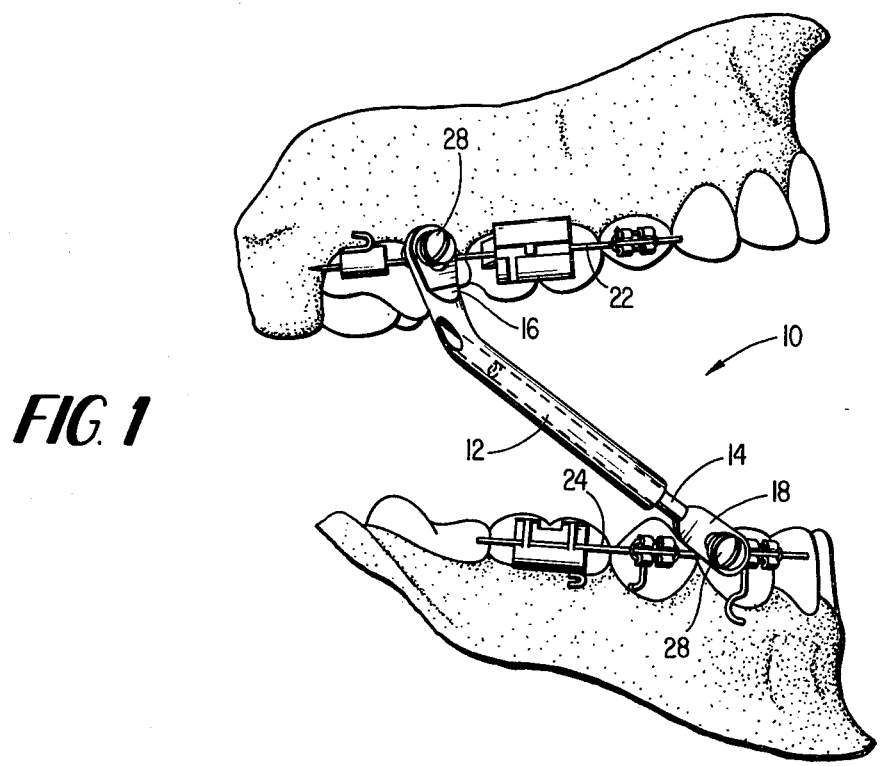
FIG. 1 is a perspective side view showing the orthodontic device of the present invention as installed in the mouth of a patient, with the mouth in the open position.

In the embodiment of the invention as shown in FIGS. 1-8, there is provided an orthodontic bite jumping device 10 having telescoping members which include outer tube portion 12 and inner plunger portion 14. The telescope tube portion 12 and plunger portion 14 are each provided with a respective ring member 16, 18 secured to the outer ends thereof. In one embodiment, ring 16 attached to the tube portion 12 extends outwardly from the tube portion 12 at an angle of approximately 45 degrees relative to the longitudinal axis of the tube 12. The ring 18 is attached to the plunger portion 14 extends directly outwardly in alignment with the longitudinal axis of the plunger portion 14. Each of the rings 16, 18 is of relatively narrow width compared to the diameter of telescope tube 12.

In the embodiment shown in FIG. 4, the telescope tube 12 and respective ring 16 are formed as a single piece construction from a suitable metal. The telescope plunger 14 and ring 18 are formed in a similar manner. The bore 40 within tube 12 extends throughout the length of the tube 12, thus allowing longitudinal movement of the plunger 14 within the entire length of the tube 12. In the device 10 as installed in the mouth of a patient, the outer end of the plunger 14 may extend outwardly beyond the bore 40 of the tube 12, and the upward slant of the ring 16 helps to avoid contact between these components during operation of the device 10.

Figure 2:
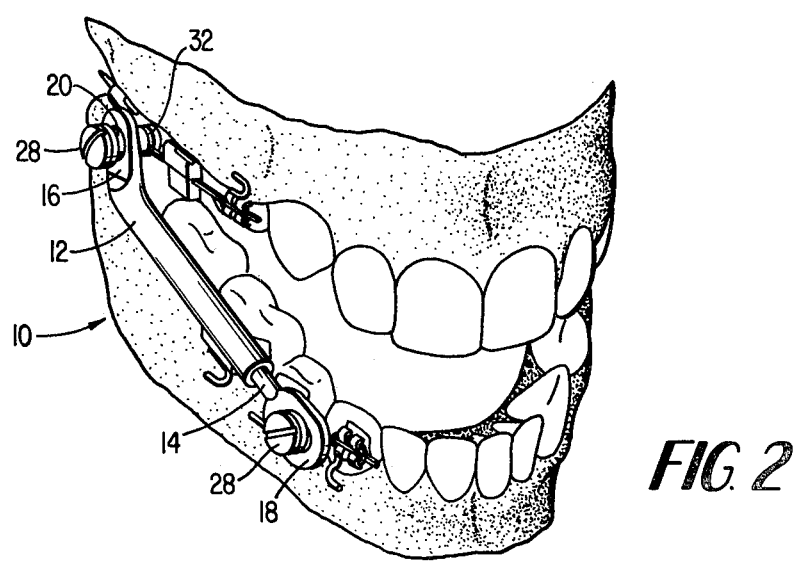
FIG. 2 is perspective view from the front of the mouth showing the device of FIG. 1 with the mouth in the open position.

A trunnion or pin member 20 is provided for attachment of the device to the orthodontic brace wires 22, 24 affixed to teeth in the upper and lower jaws of the patient. For purposes of clarity, the brace wires 22, 24 are shown in FIGS. 1-3 only in the areas adjacent the points of attachment of the device 10 of the present invention. It should be understood, however, that in actual use the brace wires 22, 24 would normally extend around the entire contour of the upper and lower jaw in a typical treatment procedure, and that a similar device 10 of the present invention would also be installed on the opposite side of the jaw.

Figure 6:
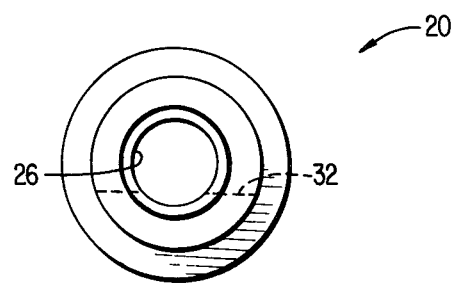
FIG. 6 is an end view of the pin member of FIG. 5.
Figure 7:
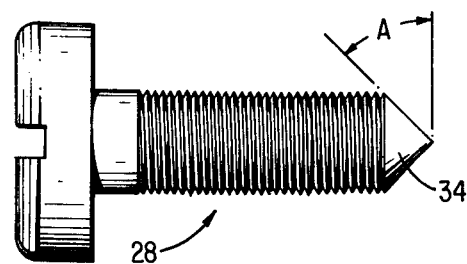
FIG. 7 is an enlarged front elevation of the screw member employed in the device of FIG. 1.
Figure 8:
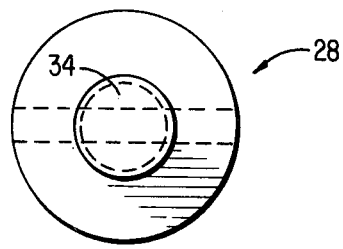
FIG. 8 is an end view of the screw member of FIG. 7.

As shown in FIGS. 5 and 6, each trunnion 20 has an axial bore 26 which extends the length of the trunnion 20. The walls of the bore 26 are threaded as shown at 27 so as to receive a threaded screw member 28 through the outer end 30 thereof. A radial slot 32 is provided adjacent the inner end of each trunnion 20. The slot 32 preferably extends radially through the trunnion 20 sufficiently far so that an orthodontic brace wire 33 positioned at the innermost end of the slot 32 will be retained in position by the tapered inner end 34 of the screw member 28. In one embodiment, the inner end 34 of the screw 28 is tapered at an angle A of approximately 45 degrees. A flange 36 on the outer end of the trunnion 20 prevents outward movement of the respective ring member 16, 18 mounted on the trunnion 20, as described hereinafter. The relationship of each trunnion 20 and the respective ring member 16 or 18 mounted thereon is such that the diameter across the opening 38 of one or both of the rings 16 or 18 is substantially greater than the diameter of the respective trunnion 20, with the result that looseness or "play" is provided in the relative movement between ring and trunnion at each end of the device 10. Such "play" is essential in allowing the device 10 to function effectively within the mouth while the patient is chewing food or carrying out other jaw movements which take place during everyday use.

Upon installing the device 10 in the mouth of a patient, the trunnions 20 are mounted on the respective brace wires 22, 24 with the upper trunnion 20 attached at the rear portion of the upper jaw while the lower trunnion 20 is attached to the forward portion of the lower jaw, as shown in FIGS. 1-3. In one method of treatment, the trunnions 20 are initially positioned so that when the telescope tube 12 and plunger 14 are closed, as shown in FIG. 3, corresponding to a closed position of the mouth, the force exerted by the upper jaw through the lower end of the tube 12 on the ring 18 and thus on the lower jaw will cause the lower jaw to be jumped anteriorly to an edge-to-edge position between the central or lateral incisors, thus placing the dental arches in a Class I or overcorrected Class I relationship with the posterior teeth out of position. As previously stated, it should of course be understood that a pair of devices 10 are generally employed, one on either side of the jaw, so as to effect a uniform treatment on each side of the mouth.

The looseness or "play" between a trunnion 20 and the respective ring member 16 or 18 at the ends of the device 10 allows the device 10 to be flexible and thus avoid being broken during use. As shown in a comparison of FIGS. 2 and 3 of the drawings, for example, the upper ring 16 is located toward the center of trunnion 20 when the jaw is open, while the ring 16 moves toward the outer end of the trunnion 20, adjacent flange 36, when the jaw is closed. The looseness between trunnion and ring provides for such movement. Such action, allowing freedom of movement of the lower jaw, has been found to result in a much more comfortable bite jumping device. in one embodiment, a desirable amount of looseness or "play" may be obtained by constructing each of the rings 16, 18 so that the diameter of the opening 38 therein is approximately 1 ¼ to 2 times the diameter of the trunnion 20. In such an embodiment, the trunnion 20 may have an overall length of 0.220 inch and a diameter of 0.120 inch. In this embodiment, the radial slot 32 has a width of 0.032 inch and a depth of 0.080 inch.

The invention may be embodied in other specific forms without departing from the spirit or essential characteristics thereof. The pesent embodiment is therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. An orthodontic bite jumping device for attachment to orthodontic brace wires affixed to the teeth of the upper and lower jaw of a patient for treatment of overbite, comprising: a telescope mechanism having a telescope outer tube portion and a telescope inner plunger position, each of said tube portion and plunger portion having a ring member with central opening attached at the outer end thereof; a pair of trunnion members, one of said trunnion members being received in the opening of each of said ring members, each trunnion member having a structurally integral flange on the outer end thereof retaining the respective ring member on the trunnion; a radial slot located in each trunnion member adjacent the inner end thereof for receiving one of said brace wires, said slot being defined by a pair of side walls and a bottom wall, said side walls being located in parallel planes which are perpendicular to the longitudinal axis of the respective trunnion, said side walls extending to the exterior of said trunnion so that said slot is open along its entire length to receive one of said brace wires; each of said trunnions having an axial bore in the outer end thereof, said bore being in communication with the espective radial slot and being substantially perpendicular thereto; and means mounted in each of said bores for securing said respective trunnion to one of said brace wires with said brace wire in position within the respective slot.

2. The orthodontic device of claim 1 wherein the diameter of the central opening of at least one of the ring members is substantially greater than the diameter of the respective trunnion, thus providing looseness or play in the relative movement between ring and trunnion at at least one end of the device.

3. The orthodontic device of claim 2 wherein the diameter of the opening in said at least one ring member is approximately 1¼ to 2 times the dimeter of the respective trunnion.

4. The orthodontic device of claim 2 wherein the diameter of the central opening of each of the ring members is substantially greater than the diameter of the respective trunnion, thus providing said looseness or play at each end of the device.

5. The orthodontic device of claim 4 wherein the diameter of the opening in each of the ring members is approximately 1¼ to 2 times the diameter of the respective trunnion.

6. The orthodontic device of claim 1 wherein said means for securing said trunnion comprises a screw member which is threadedly received in the axial bore, said screw member extending into the respective radial slot when the brace wire is in position in said slot.

7. An orthodontic bite jumping device for attachment to orhtodontic brace wires affixed to the teeth of the upper and lower jaw of a patient for treatment of overbite, comprising: a telescope mechanism having a telescope outer tube portion and a telescope inner plunger portion, each of said tube portion and plunger portion having a ring member with central opening attached at the outer end thereof; a pair of trunnion members, one of said trunnion members being received in the opening of each of said ring members; a radial slot located in each trunnion member adjacent the inner end thereof for receiving one of said brace wires; each of said trunnions having an axial bore in the outer end thereof, said bore being in communication with the respective radial slot; and means mounted in each of said bores for securing said respective trunnion to one of said brace wires with said brace wire in position within the respective slot, the diameter of the central opening of at least one of the ring members being substantially greater than the diameter of the respective trunnion, thus providing looseness or play in the relative movement between ring and trunnion at at least one end of the device.

8. The orthodontic device of claim 7, wherein the diameter of the opening in said at least one ring member is approximately 1¼ to 2 times the diameter of the respective trunnion.

9. The orthodontic device of claim 7, wherein the diameter of the central opening of each of the ring members is substantially greater than the diameter of the respective trunnion, thus providing said looseness or play at each end of the device.

10. The orthodontic device of claim 9, wherein the diameter of the opening in each of the ring members is approximately 1¼ to 2 times the diameter of the respective trunnion.

11. The orthodontic device of claim 7, wherein the means for securing said trunnion comprises a screw member which is threadedly received in the axial bore, said screw member extending into the respective radial slot when the brace wire is in position in said slot.

12. The orthodontic device of claim 7, wherein each trunnion member has a flange on the outer end thereof for use in retaining the respective ring member on the trunnion.

13. An orthodontic bite jumping device for attachment to orthodontic means affixed to the teeth of the upper and lower jaw of a patient for treatment of overbite, comprising: a telescope mechanism having a telescope outer tube portion and a telescope inner plunger portion, each of said tube portion and plunger portion having a ring member with central opening attached at the outer end thereof; a pair of trunnion members, one of said trunnion members being received in the opening of each of said ring members; and means for mounting each trunnion member on said orthodontic means; the diameter of the central opening of at least one of the ring members being substantially greater than the diameter of the respective trunnion, such that the diameter of the opening is said at least one ring member is approximately 1¼ to 2 times the diameter of the respective trunnion, thus providing looseness or play in the relative movement between ring and trunnion at at least one end of the device.

14. The orthodontic device of claim 13, wherein the diameter of the central opening of each of the ring members is substantially greater than the diameter of the respective trunnion, thus providing said looseness or play at each end of the device.

15. The orthodontic device of claim 14 wherein the diameter of the opening in each of the ring members is approximately 1¼ to 2 times the diameter of the respective trunnion.

* * * * *